United States Patent [19]

O'Kennedy et al.

[11] Patent Number: 5,392,643
[45] Date of Patent: Feb. 28, 1995

[54] OXYGEN HEATER SENSOR DIAGNOSTIC ROUTINE

[75] Inventors: Maura P. O'Kennedy, Livonia; Min Sway-Tin, Troy; Martin G. Yagley, Sterling Heights; Anson Lee, St. Clair, all of Mich.

[73] Assignee: Chrysler Corporation, Highland Park, Mich.

[21] Appl. No.: 155,673

[22] Filed: Nov. 22, 1993

[51] Int. Cl.6 .......................................... G01M 15/00
[52] U.S. Cl. ................................................ 73/118.1
[58] Field of Search ............... 73/118.1, 1 G; 123/688

[56] References Cited

U.S. PATENT DOCUMENTS

| | | |
|---|---|---|
| 4,121,548 | 10/1978 | Hattori et al. . |
| 4,167,163 | 9/1979 | Moder et al. . |
| 4,172,432 | 10/1979 | Wessel et al. . |
| 4,177,787 | 12/1979 | Hattori et al. . |
| 4,178,793 | 12/1979 | Bremer et al. . |
| 4,208,993 | 6/1980 | Peter . |
| 4,214,308 | 7/1980 | Carp . |
| 4,214,563 | 7/1980 | Hosaka . |
| 4,223,549 | 9/1980 | Kitzinger . |
| 4,252,098 | 2/1981 | Tomczak et al. . |
| 4,430,191 | 2/1984 | Sone et al. . |
| 4,450,812 | 5/1984 | Otsuka et al. . |
| 4,450,815 | 5/1984 | Mouri . |
| 4,492,205 | 1/1985 | Jundt et al. . |
| 4,570,069 | 2/1986 | Gager . |
| 4,663,717 | 5/1987 | Kobayashi et al. . |
| 4,671,243 | 6/1987 | Deutsch . |
| 4,724,814 | 2/1988 | Mieno et al. . |
| 4,742,808 | 5/1988 | Blumel et al. . |
| 4,759,328 | 7/1988 | Blumel et al. . |
| 4,819,602 | 4/1989 | Mieno et al. . |
| 4,844,038 | 7/1989 | Yamato et al. . |
| 4,868,508 | 9/1989 | Ohishi . |
| 4,938,194 | 7/1990 | Kato et al. . |
| 4,951,632 | 8/1990 | Yakuwa et al. . |
| 4,958,611 | 9/1990 | Uchinami et al. . |
| 5,020,499 | 6/1991 | Kojima et al. . |
| 5,054,452 | 10/1991 | Denz . |
| 5,091,698 | 2/1992 | Grabs . |
| 5,096,565 | 3/1992 | Kaganov . |
| 5,111,792 | 5/1992 | Nagai . |

Primary Examiner—Richard E. Chilcot, Jr.
Assistant Examiner—Harshad Patel
Attorney, Agent, or Firm—Wendell K. Fredericks

[57] ABSTRACT

A diagnostic method is provided for sensing whether an oxygen sensor is still suitable for use in measuring the fuel-air mixture in the exhaust gases of an internal combustion engine. The method involves turning off a heater of an oxygen sensor when the engine is turned off and allowing the sensor to cool. While the sensor cools, the sensor resistance is measured by means of a large pull-up resistor and a small pull-up resistor, with the small resistor being switched into the circuit at regular intervals for a short period of time. The use of the small pull-up resistor not only increases the reliability of the measurements, but also aids in quickly determining when the sensor resistance has increased above a threshold value indicating the sensor is cool. When the sensor is sufficiently cool, the heater is turned on and the sensor is monitored for a decrease in resistance, indicating that the heater is functioning properly.

23 Claims, 2 Drawing Sheets

OXYGEN HEATER SENSOR DIAGNOSTIC ROUTINE

BACKGROUND OF THE INVENTION

The invention relates to a heated oxygen sensor diagnostic routine and, more particularly to a diagnostic routine performed to ascertain whether an automotive oxygen sensor is still suitable for use.

Oxygen sensors are employed in most modern internal combustion engines for monitoring the by-products of combustion in order to regulate the fuel-air mixture. A properly regulated air fuel mixture is necessary to achieve clean burning of the fuel. Achieving a clean burn is especially important in an automotive engine, where strict emissions standards are difficult to meet if the fuel is not cleanly burned.

The sensor generates an output voltage depending on the content of oxygen in the fuel-air mixture at the exhaust. If the exhaust gas is rich in oxygen, the sensor will produce a low voltage, close to zero volts. If the exhaust gas is rich in fuel, the sensor will produce a voltage close to one volt.

The output voltage and internal resistance of the sensor will also vary with the temperature and the age of the sensor. The internal resistance can vary from about 100 ohms to several million ohms depending on the temperature of the sensor. A cold sensor has a very high internal resistance, which drastically decreases once the sensor reaches an operating temperature of about 300 degrees Celsius.

Because of its high internal resistance when cold, the sensor is lean in $O_2$ or unreliable during the engine warm-up phase. During this period the engine operates in an open loop where data from the sensor is not used to regulate the fuel mixture. Since it is highly desirable to reach a closed loop condition rapidly, where data from the sensor is used to regulate the fuel mixture, a heater may be included in the automotive oxygen sensor as shown in U.S. Pat. No. 4,938,194 to Kato et. al. The heater brings the sensor to its operating temperature faster than it would if heated by the engine exhaust gases alone. Thus, the heater allows the engine to reach closed loop operation more rapidly.

The oxygen sensor becomes less reliable with age, because physical wear and chemical contamination affect the output voltage and internal resistance of the sensor. With a failed oxygen sensor the engine will run inefficiently, taking a serious toll on the performance of the car.

In addition, operating an automobile with a failed oxygen sensor can have a significant environmental impact. The amount of air pollutants produced by the automobile will increase directly due to an unclean burn, and also indirectly due to the failure of the catalytic converter when it receives large quantities of unburned fuel. Furthermore, a failed sensor can increase fuel consumption, turning a normally efficient fuel consuming car into a gas guzzler.

When the sensor fails, the automobile owner typically does not suspect the oxygen sensor, or may not even be aware that the automobile has an oxygen sensor. In addition to the possible expense incurred when the car fails to meet optimal emission levels, the owner is put to the unnecessary expense of having a mechanic troubleshoot the car to determine that the sensor has in fact failed. Often unnecessary work will be performed by an inexperienced mechanic who does not know to check the oxygen sensor heater to see if it has failed.

When the heater fails, closed loop operation cannot be achieved until the oxygen sensor has been heated sufficiently by the engine exhaust to the sensor's optimal operating temperature. Depending on the driving conditions, this time period can vary tremendously. While the oxygen sensor is warming up, and the engine is in open loop operation, the engine will perform inefficiently, since the fuel-air mixture will be less than optimum and may not meet today's emissions standards. It is therefore highly desirable to know whether the heater is still functional.

U.S. Pat. No. 4,742,808 to Blümel ('808) discloses a means and method for measuring the internal resistance of an oxygen sensor using two resistors. These resistors are alternately switched into the measuring circuit to obtain reliable measurements—reliable in the sense that two measurements are better than one. The test in the '808 patent determines if the sensor is ready for closed loop operation and does not detect wear or inoperability of the sensor. Further, the two resistors used in the '808 patent are not indicated as being of substantially different impedances, which would allow one to be used to quickly detect changes in the oxygen sensor internal impedance.

U.S. Pat. No. 4,844,038 to Yamato et. al. ('038) discloses a method for determining the deterioration of oxygen concentration sensors. The '038 patent diagnoses a sensor as abnormal if the output signal of the sensor remains substantially constant for a predetermined length of time. Thus, it does not provide a means for quickly detecting changes in sensor impedance.

SUMMARY OF THE INVENTION

It is an object of the present invention to perform a diagnostic routine that will determine the internal resistance of an oxygen sensor near its operating temperature.

It is another object of the invention to perform a diagnostic routine to determine if the heater in an oxygen sensor is still operational.

It is a further object of the invention to perform a diagnostic routine that will detect the failure, or impending failure of an oxygen sensor.

It is a still further object of the invention to perform a diagnostic routine on a heated oxygen sensor that can be conducted rapidly and without damaging the sensor.

According to an illustrative embodiment of the present invention, a diagnostic routine for sensing whether an oxygen sensor is still suitable for use involves turning off the heater of an oxygen sensor when the engine has been shut off, thus allowing the sensor to cool. While the sensor cools, the sensor resistance is measured. This is accomplished by supplying a voltage to the sensor through a large pull-up resistor and measuring the voltage across the sensor. A small pull-up resistor connected to a further voltage is switched into parallel with the large resistor in the circuit at regular intervals for a short period of time. The use of the small pull-up resistor not only increases the reliability of the measurements, but also aids in quickly determining when the sensor resistance has increased above a threshold value indicating that the sensor is cool. This is due to the fact that the smaller pull-up resistance makes the sensor output voltage relatively larger, so that small changes in the sensor internal resistance, which are reflected by changes in the sensor voltage, can be seen more easily.

When the sensor is sufficiently cool, the heater is turned on and the sensor is monitored for a decrease in resistance, indicating that the heater is functioning properly.

BRIEF DESCRIPTION OF THE DRAWINGS

The foregoing and other features of the present invention will be more readily apparent from the following detailed description of preferred embodiments taken in conjunction with the attached drawings wherein:

FIG. 4b is a graphical representation of the state of the heater (on or off) along the same time line as FIG. 4a.

DETAILED DESCRIPTION OF THE PREFERRED EMBODIMENT

Figure 1:
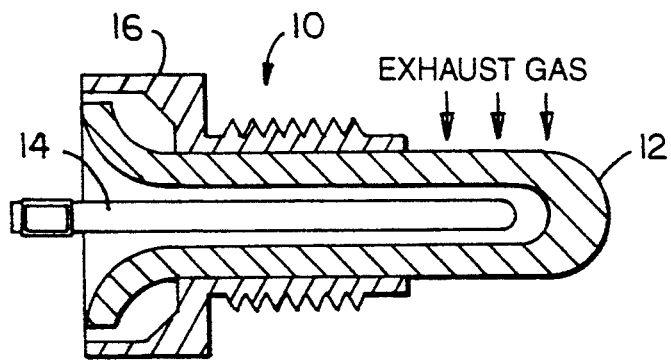
FIG. 1 is a diagrammatic view of a prior art heated oxygen sensor which may be analyzed by the present invention.

FIG. 1 illustrates a heated oxygen sensor 10. The sensor 10 has a sensor element 12 for detecting the presence of oxygen in the exhaust of an engine. The sensor 10 is heated to a suitable operating temperature by a heater element 14. The sensor 10 has a threaded body 16, for threading into the exhaust manifold of an engine.

Figure 2:
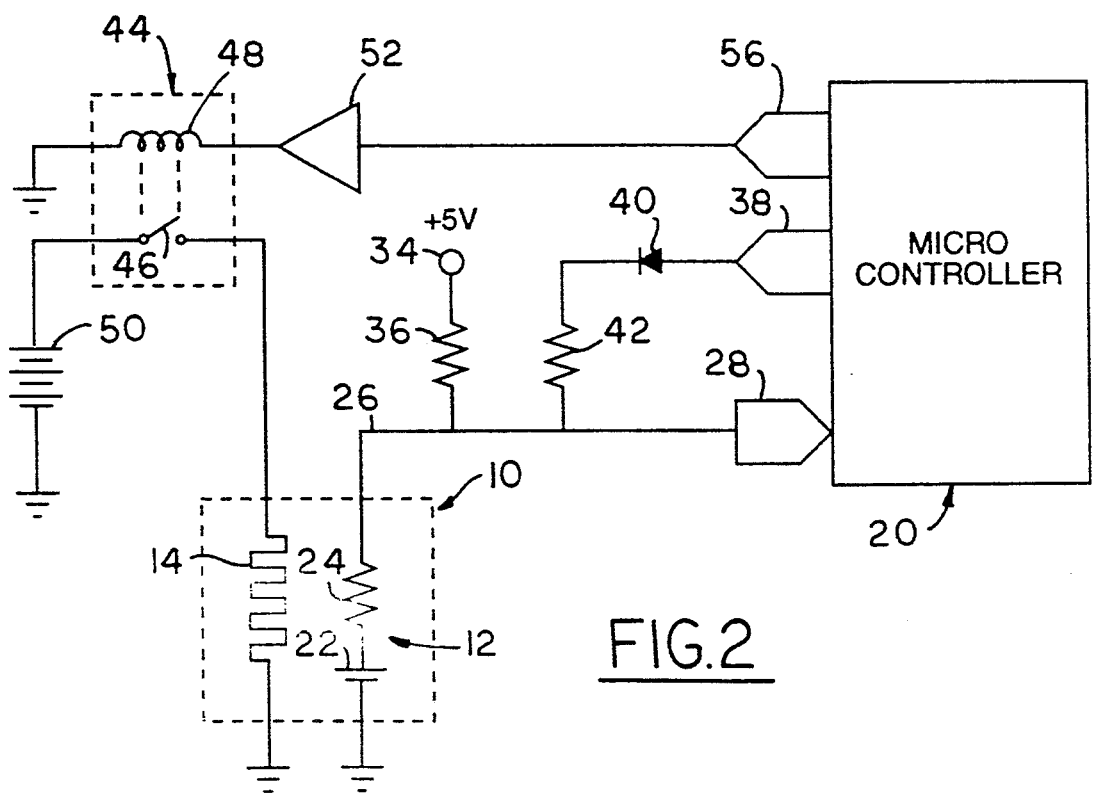
FIG. 2 is a circuit diagram of the interconnection of the oxygen sensor with an engine controller, for practicing the diagnostic routine of the present invention.

FIG. 2 illustrates the interconnection of the oxygen sensor 10 with an engine controller 20. The sensor element 12 may be represented by a Thevenin equivalent voltage source 22 having a voltage Vs, in series with a Thevenin equivalent resistance 24 having a variable resistance Rs. The sensor element 12 is connected between a sensor output 26 and ground.

The sensor output 26 is connected to an A/D converting input 28 of the engine controller 20. The sensor output 26 is biased by a large pull-up resistor 36 having a resistance R1 connected to a power supply 34 having a voltage VCC, e.g. 5 volts. The value for the large pull up resistor 36 may be, for example, two million ohms.

The sensor output may also be biased by an output port 38 on the engine controller 20. This output port 38 is selectively switchable between a 0 volt and, e.g., a 5 volt output. The output port 38 is connected to the sensor output 26 through a diode 40 and a small pull-up resistor 42 having a resistance R2. Small pull-up resistor 42 may have a value of, e.g., 100K ohms, and the diode 40 should have low-leakage characteristics. The diode 40 is oriented so that it will allow a current to flow from output port 38 through the small pull-up resistor 42 of the sensor output 26 if the output port 38 has, e.g., a 5 volt output.

A relay 44, has a relay switch 46 and a relay coil 48. The relay switch 46 is operated by the relay coil 48. The relay switch 46 is in the closed position when the relay coil 48 is energized. Heater element 14 is connected to a battery 50 through the relay switch 46 and relay coil 48 is connected to a heater control port 56 on the engine controller 20 through a driver 52. The driver 52 can be a transistor integrated circuit driver, or any other device that can produce sufficient output current, in response to a low current output from heater control port 56, to energize the relay coil 48. When the heater control port 56 is enabled, the driver 52 is turned on, energizing the relay coil 48 and closing the relay switch 46. When the relay switch 46 is closed, the heater element 14 is connected to the battery 50, and heats the sensor element 12.

During normal engine operation, the circuit operates as follows:

The heater control port 56 is enabled, thereby turning on the driver 52. The driver 52 allows a current to flow through the relay coil 48, energizing the relay coil 48, and thereby closing the relay switch 46. The relay switch 46, in its closed position, allows a current to flow through the heater element 14 from battery 50, which heats the sensor 10.

When the sensor 10 is ready for closed loop operation, the engine controller 20 monitors the output voltage of the sensor output 26 through the A/D converting input 28. The output port 38 is at a low logic voltage of approximately zero volts, so the diode 40 is not forward biased, and does not conduct current. Consequently, there is virtually no current flowing through the small pull-up resistor 42.

When the engine is shut-off, or the exhaust gas is diverted from the oxygen sensor, the diagnostic routine of the present invention begins. The heater control output 56 is disabled, turning off the driver 52, which in turn de-energizes the relay coil 48. The heater element 14 is thus shut off. With the heater element 14 shut off, and the exhaust gas no longer heating the oxygen sensor, the oxygen sensor cools.

To determine the internal resistance of the oxygen sensor 10, the sensor output 26, biased by the large pull-up resistor 36 and the 5 volt supply 34, is measured with the A/D converting input 28. This value is stored as value V1. One skilled in the art will recognize that the internal resistance Rs of the oxygen sensor 10 is proportional to the value V1, and of course the reverse is also true. In the present embodiment:

$$Rs = \frac{R1 * (Vs - V1)}{(V1 - VCC)} \text{ and} \quad (1)$$

$$V1 = \frac{[Rs * (VCC - Vs)]}{(R1 + Rs)} + Vs \quad (2)$$

where VCC is the 5 volts. level signed at terminal 34.

The output port 38 is then brought to a logic high, where it has a voltage of approximately 5 volts. The diode 40 is forward biased, and a current flows through the small pull-up resistor 42. Sensor output 26 is now biased by both pull-up resistors and their respective voltage supplies. After a short period of time sufficient for stabilization, perhaps 35 milliseconds, the sensor output 26 is measured with the A/D converting input 28. This value is stored as value V2. One skilled in the art will recognize that the internal resistance Rs of the oxygen sensor 10 is proportional to value V2. In the present embodiment, substituting the equivalent of resistors R1 and R2 in parallel, i.e.

$$\frac{R1 * R2}{R1 + R2},$$

into equation (1) and (2) yields:

$$Rs = \frac{(R1 * R2) * (Vs - V2)}{(R1 + R2) * (V2 - VCC)} \text{ and} \qquad (3)$$

$$V2 = \frac{Rs * (VCC - Vs) * (R1 + R2)}{(R1 * R2) + [Rs * (R1 + R2)]} + Vs \qquad (4)$$

After the measurement of V2 is made, the output port 38 is immediately disabled, bringing it back to a low logic voltage. The diode 40 will not be forward biased, and virtually no current will flow through the small pull-up resistor 42. It is important that the output port 38 be on for only a short time, since a relatively larger current flows through the sensor when current is allowed to flow through the small pull-up resistor 42 when the output port 38 is turned on. Allowing a relatively large current to flow through the sensor for a prolonged period of time will cause "blackening" of the sensor element 12, which will shorten its useful life.

The resistance of the sensor 12 is proportional to the difference between measured values V1 and V2. The difference between V1 and V2 is stored as an initial delta reference voltage in controller 20. An absolute sensor resistance, while the sensor is near its normal operating temperature, can be calculated from V1, V2 and the initial delta reference voltage, using known values for the small pull-up resistor 42 and the large pull-up resistor 36. This absolute sensor resistance is useful in monitoring changes in the sensor resistance with the aging of the sensor, for possible recalibration or early detection of approaching failure.

If the initial delta reference voltage exceeds a predetermined threshold voltage, preferably about 1.5 volts, the remaining portion of the heater test is aborted. An initial delta reference voltage above the predetermined threshold voltage would tend to indicate that the sensor did not reach a sufficiently high temperature prior to the engine being shut-off for the heater test to be effective. For example, if the engine was only running for a short period of time, the sensor would not be sufficiently heated for it to be tested effectively.

Figure 3:
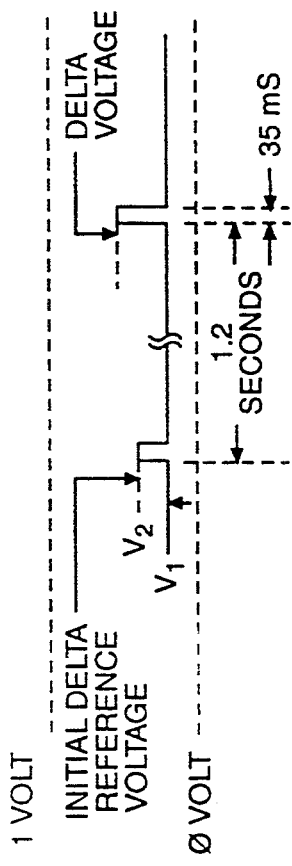
FIG. 3 is a graphical representation of the sensor output voltage during a measurement cycle of the diagnostic routine of the present invention.
Figure 4A:
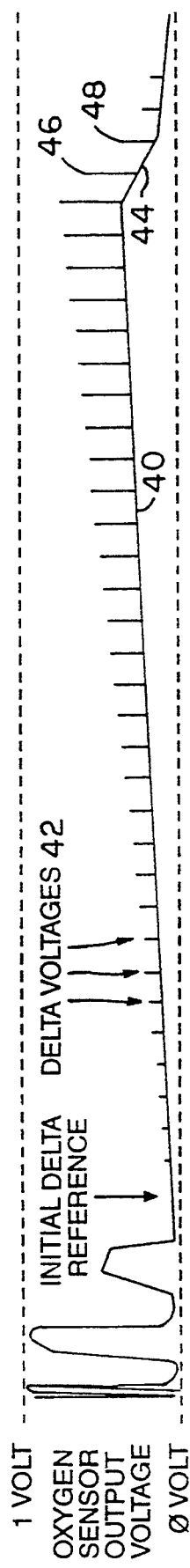
FIG. 4a is a graphical representation of the sensor output voltage during the diagnostic routine of the present invention.
Figure 4B:
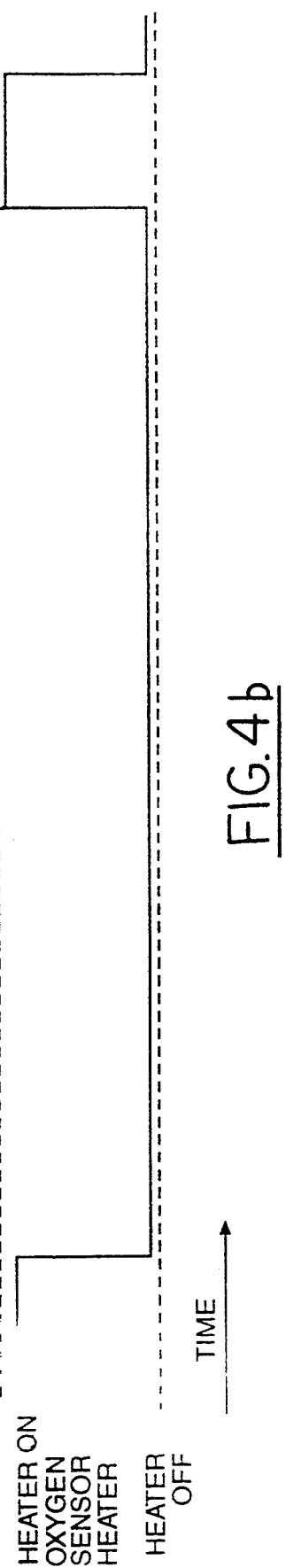

If the initial delta reference voltage is not over the predetermined threshold voltage, the cooling of the sensor is monitored, by measuring V1 and V2 at a regular interval, preferably every 1.2 seconds. A cycle of measurements is shown in FIG. 3, where the measured sensor output voltage is shown as a function of time for a measurement cycle. For each measurement cycle, the difference between V1 and V2 is determined as a delta voltage. In general, after the engine and the heater have been shut off, the sensor voltage should increase, since the sensor is cooling. As the sensor resistance increases, the delta voltage should also increase. FIG. 4a and 4b illustrate how the sensor output voltage 40 and the delta voltage 42 gradually increase as the sensor cools, after the heater has been shut off.

Switching the small pull-up resistor into the circuit shortens the test period, minimizing battery drain. In particular, a faster determination as to whether the sensor voltage has increased significantly can be made using the small pull-up resistor, rather than the large one, i.e. the rate of change in the measured voltage will be greater using a smaller pull-up resistor.

When the delta voltage exceeds the initial delta reference voltage by a predetermined voltage, preferably about 0.5 volts, the sensor has cooled significantly to begin testing the functionality of the heater. This is achieved by energizing the heater by enabling the heater control port 56.

Referring to FIGS. 4a and 4b, as the sensor is heated, the internal resistance should decrease as shown at 44. After a time interval, V1 and V2 are measured again, and a new or second series of delta voltages 46, 48 is determined by subtracting V1 from V2. If the heater is functioning, the sensor output voltage 44, and also, the second series of delta voltages 46, 48 should begin to decrease. The second measurement of the delta voltage 48 should be lower than the delta voltage 46 measured just after the time when the heater was turned on at 50. This indicates, that the sensor resistance has decreased. If the sensor resistance has decreased since the heater was turned on at 50, the heater is probably functioning properly.

To avoid incorrect diagnosis due to noise, several measurement cycles of the second delta voltage can be conducted at regular intervals, perhaps every 1.2 seconds. If the trend of these measurements tends to show a relatively steady decrease in the delta voltage, the sensor resistance is decreasing, and the heater is functioning. If the voltage does not decrease appreciably, the heater is probably no longer functional.

While the invention has been particularly shown and described with reference to preferred embodiments thereof, it will be understood by those skilled in the art that various changes in form and details may be made therein without departing from the spirit and scope of the invention.

What is claimed is:

1. An oxygen sensor heater diagnostic method for diagnosing the condition of an oxygen sensor having a heater and located to intercept the exhaust gases from an engine, comprising the steps of:
   shutting off the heater;
   preventing the exhaust gas of the engine from heating the oxygen sensor;
   measuring a first output voltage of the sensor at a sensor output as a value V1 when connected to a supply voltage through a large pull-up resistor;
   measuring a second output voltage of the sensor at a sensor output as a value V2 when connected to a first predetermined voltage through a small pull-up resistor;
   determining an initial delta reference voltage by subtracting V1 from V2;
   using said initial delta reference voltage to indicate the sensor internal resistance as of the measurements; and
   monitoring the magnitude of the initial delta reference voltage.

2. The diagnostic method of claim 1, wherein the step of using said initial delta reference voltage comprises the step of:
   determining the sensor internal resistance from the magnitude of the initial delta reference voltage, and the resistance values of the pull-up resistors.

3. The diagnostic method of claim 2, further comprising the steps:
   repeating the measurements of V1 and V2 to find at least one subsequent delta voltage for determining a subsequent sensor internal resistances as of such measurement; and
   monitoring the initial and subsequent sensor internal resistance for an increase in resistance as an indication that the sensor resistance is increasing as the sensor cools and the sensor is operating properly.

4. The diagnostic method of claim 3, wherein the step of repeating occurs repetitively.

5. The diagnostic method of claim 4, wherein the step of repeating occurs approximately every 1.2 seconds.

6. The diagnostic method of claim 5, wherein the limited period of time is about 35 milliseconds.

7. The diagnostic method of claim 3 further including the steps of:
- checking to see if the subsequent delta voltages exceed the initial delta reference voltage by a second predetermined voltage;
- energizing the heater when the second predetermined voltage is exceeded;
- taking continuous measurements of V1 and V2 to find further delta voltages; and
- monitoring the further delta voltages for a decrease in magnitude as an indication that the heater is functional.

8. The diagnostic method of claim 7, wherein the second predetermined voltage is approximately 0.5 volts.

9. The diagnostic method of claim 1, wherein during the step of measuring the second output voltage, the small pull-up resistor is connected to the first predetermined voltage for a limited period of time.

10. The diagnostic method of claim 9, wherein the step of measuring the second output voltage, comprises the steps of:
- switching the small pull-up resistor in to the measuring circuit;
- waiting a short period of time for the second sensor output voltage to stabilize;
- measuring, as value V2, the sensor output voltage; and
- switching the small pull-up resistor out of the measuring circuit sufficiently quickly to prevent blackening of the sensor from the prolonged presence of a relatively large current in the sensor.

11. The diagnostic method of claim 10, wherein the steps of switching the small pull-up resistor, comprises the steps of:
- connecting one end of the small pull-up resistor to the sensor output;
- connecting the other end of the small pull-up resistor through a diode to a switchable voltage source; and
- switching the switchable voltage source on in order to switch said small pull-up resistor in to the measuring circuit and switching the switchable voltage source off so as to back biasing the diode in order to switch said small pull-up resistor out of the measuring circuit.

12. The diagnostic method of claim 1, wherein the large pull-up resistor is approximately two million ohms and the small pull-up resistor is approximately one hundred thousand ohms.

13. The diagnostic method of claim 1, further comprising the step of:
- aborting the test if the magnitude of the initial delta reference voltage exceeds a threshold voltage.

14. The diagnostic method of claim 13, wherein the threshold voltage is approximately 1.5 volts.

15. The diagnostic method of claim 1, wherein the first predetermined voltage and supply voltage are equal.

16. The diagnostic method of claim 1, wherein the step of preventing the exhaust gas comprises shutting the engine off.

17. An oxygen sensor heater diagnostic method, for diagnosing the condition of an oxygen sensor having a heater and used in an automobile engine to intercept the exhaust gases from the engine and provide a measurement of the fuel-air mixture, comprising the steps of:
- turning off the heater;
- preventing the exhaust gas of the engine from heating the sensor;
- measuring a voltage V1 when the sensor is connected through a large pull-up resistor to a first source of voltage and a voltage V2 when the sensor is connected through a small pull-up resistor to a second source of voltage to determine an initial delta reference voltage, that is, the difference between V1 and V2, which is proportional to the sensor internal resistance;
- repeatedly measuring a first series of delta voltages until the delta voltage exceeds the initial delta reference voltage by a predetermined level;
- turning the heater on;
- measuring a second series of delta voltages;
- comparing the magnitudes of the delta voltages in the second series of delta voltages; and
- determining the heater is functioning if the delta voltages of the second series of delta voltages are decreasing and determining the heater is not functioning if they are not.

18. The sensor diagnostic method of claim 17, wherein the step of preventing the exhaust gas comprises shutting the engine off.

19. A sensor diagnostic method for diagnosing the condition of an oxygen sensor having a heater, comprising the steps of:
- allowing the sensor to cool;
- energizing the heater;
- repeatedly measuring a voltage V1 when the sensor is connected through a large pull-up resistor to a first source of voltage and a voltage V2 when the sensor is additionally connected for a short period of time through a small pull-up resistor to a second source of voltage;
- determining a series of delta reference voltages by subtracting the repeated voltages of V1 and V2, and
- monitoring the magnitude of the delta reference voltages to determine whether they are decreasing, as an indication that the heater of the sensor is operating properly.

20. The method of claim 19, wherein the repeated measuring occurs at the rate of about once every 1.2 seconds.

21. The method of claim 19, wherein the large pull-up resistor is about the million ohms, the small pull-up resistor is about one hundred thousand ohms and the first and second sources of voltages are about five volts.

22. The method of claim 19, wherein the short period of time is sufficient to prevent blackening of the sensor.

23. The method of claim 22, wherein the short period of the is about 35 milliseconds.

* * * * *